(12) United States Patent
Leevan et al.

(10) Patent No.: US 9,974,913 B2
(45) Date of Patent: May 22, 2018

(54) RESPIRATION MASK INTERFACE SEAL

(71) Applicant: Gemguardian, LLC, Fox Point, WI (US)

(72) Inventors: Yakira Leevan, Fox Point, WI (US); Rachel Goldman, Milwaukee, WI (US)

(73) Assignee: GEMGUARDIAN, LLC, Fox Point, WI (US)

( * ) Notice: Subject to any disclaimer, the term of this patent is extended or adjusted under 35 U.S.C. 154(b) by 264 days.

(21) Appl. No.: 14/508,134

(22) Filed: Oct. 7, 2014

(65) Prior Publication Data

US 2015/0027447 A1    Jan. 29, 2015

Related U.S. Application Data (60) Provisional application No. 61/969,372, filed on Mar. 24, 2014.

(51) Int. Cl.
*A61M 16/06* (2006.01)

(52) U.S. Cl.
CPC .  *A61M 16/0605* (2014.02); *A61M 2016/0661* (2013.01); *A61M 2205/02* (2013.01); *A61M 2207/00* (2013.01); *A61M 2210/04* (2013.01); *A61M 2210/0618* (2013.01); *A61M 2210/0625* (2013.01); *Y10T 156/1002* (2015.01)

(58) Field of Classification Search
CPC ...... A61M 16/0605–16/0627; A61M 16/0688; A61M 2106/0661
See application file for complete search history.

(56) References Cited

U.S. PATENT DOCUMENTS

| | | | | |
|---|---|---|---|---|
| 6,082,360 A | * | 7/2000 | Rudolph | A61M 16/06 128/206.24 |
| 6,196,223 B1 | * | 3/2001 | Belfer | A41D 13/1176 128/205.25 |
| 7,152,601 B2 | * | 12/2006 | Barakat | A41D 13/1176 128/206.14 |
| 2002/0185134 A1 | * | 12/2002 | Bishop | A41D 13/1176 128/206.25 |
| 2003/0136410 A1 | * | 7/2003 | Matich | A62B 18/08 128/206.25 |
| 2004/0244799 A1 | | 12/2004 | Landis | |
| 2005/0139217 A1 | * | 6/2005 | Chiam | A41D 13/11 128/206.19 |
| 2006/0005837 A1 | * | 1/2006 | Thornton | A61M 16/06 128/205.25 |
| 2008/0302365 A1 | * | 12/2008 | Cohen | A61M 16/06 128/206.12 |
| 2009/0293880 A1 | * | 12/2009 | Rutan | A61B 5/097 128/206.21 |

(Continued)

*Primary Examiner* — Valerie L Woodward
(74) *Attorney, Agent, or Firm* — Boyle Fredrickson, S.C.

(57) ABSTRACT

A seal device or gasket assembly usable with respiration or ventilation mask systems and that is preferably at least one of adhesive or deformable. The gasket is disposed between the mask and the wearer and reduces the escape of respiration gases between the perimeter edge interface of the mask with the anatomy of the wearer and limits exposure of the epidermis located within the perimeter of the mask and between the mask and the wearer to the respiration gas flows. The mask system is particularly useful for improving communication of the respiration gases for those wearers having facial hair, abnormal dontia, and/or other abnormal facial features.

20 Claims, 8 Drawing Sheets

(56) References Cited

U.S. PATENT DOCUMENTS

| | | | |
|---|---|---|---|
| 2011/0005524 A1* | 1/2011 | Veliss | A61M 16/0666 128/206.24 |
| 2011/0132375 A1* | 6/2011 | Thornton | A61M 16/06 128/206.24 |
| 2011/0209701 A1* | 9/2011 | Derringer | A61M 16/06 128/202.17 |
| 2012/0055485 A1* | 3/2012 | Anthony | A61M 16/06 128/207.18 |
| 2012/0180795 A1* | 7/2012 | Knight | A41D 13/0556 128/206.24 |
| 2013/0074845 A1* | 3/2013 | Smith | A61M 16/06 128/205.25 |

\* cited by examiner

RESPIRATION MASK INTERFACE SEAL

CROSS-REFERENCE TO RELATED APPLICATIONS

This application claims priority to U.S. Provisional Patent Application Ser. No. 61/969,372 filed on Mar. 24, 2014 titled "Respiration Mask With Interlace Seal" and the disclosure of which is expressly incorporated herein.

BACKGROUND OF THE INVENTION

The present invention relates generally to the use of respiration or ventilation masks and, more specifically, to interfacial seal assemblies configured to be disposed between a respiration mask and the facial features of a wearer in a manner that reduces leakage associated with the area or interface between a perimeter edge of a mask and the anatomy or physical structure of the wearer and reduces agitation of the dermis or respiration flow passages such as the nasal mucosa during non-intubation positive pressure respiration assistance.

Respiration masks have various uses or applications in various arts including various medical and industrials fields. In the medical arts, respiration or ventilation masks can be used in resuscitation, sleep apnea devices, respiration monitoring, anesthesia, etc. Various industrial environments, particularly those where airborne particulate or chemicals are present, also commonly require utilization of respiration masks. It is appreciated that the performance of such respiration masks depends largely on the ability to limit, regulate and/or control exposure or communication between the respiration path and atmosphere.

One aspect related to the performance of such systems is the ability to provide a substantially or entirely sealed interface between the perimeter edge of the mask and the adjacent anatomy or features of the wearer. Although some applications require a fairly robust sealed cooperation, such as firefighting and working in environments with dangerous chemicals or particulates, other applications allow for a degree of sealed cooperation that is less than absolute. Sleep apnea is one such application wherein an absolute sealed interaction is not absolutely necessary but wherein the desired performance of the apnea device can be detrimentally affected by insufficient degrees of sealed interaction between the mask and the anatomy or features of the wearer.

The degree of facial hair a wearer prefers to display must also be considered in many respiration mask applications. Although some mask configurations and applications will tolerate a small degree of facial hair, increased amounts and lengths of facial hair can detract from the sealed interaction between the mask and the wearer. In anesthesia and sleep apnea applications, such facial hair is commonly not tolerated during utilization of the underlying device as too much of the respiration flow escapes the respiration path and thereby the patient or wearer via an unacceptable or poor degree of "sealed" cooperation of the mask with the anatomy of the wearer.

Reduced or abnormal facial structure can also detract from the ability to generate a desired degree of sealed interaction between the respiration or ventilation mask and the underlying patient or wearer. For instance, reduced dontia, mandible, or other dental or anatomical anomalies can result in ill-suited or undesirable cooperation of a conventional generally somewhat conically shaped respiration masks with the mouth and nasal area of a wearer in a manner that generates a desired degree of sealed interaction of the respiration mask with the wearer.

Prolonged periods of exposure to the respiration gases or interaction with respiration mask appliances can also present undesired consequences associated with the extended use of respiration masks. Endotracheal intubation is considered inappropriate in many applications such as where a user suffers from an obstructive airway or other airflow limitation, acute respiratory failure or distress system, obesity hypoventilation syndrome, cardiogenic pulmonary edema, onset respiratory failure during perioperative periods, those patients that experience difficulty weaning from invasive mechanical ventilator support, etc. Appropriate or desired noninvasive ventilator assistance allows many patients to avoid the discomfort and risk of injury or infection associated with invasion ventilation, such as intubation.

Obstructive sleep apnea (OSA) is a common type of sleep apnea and is caused by obstruction of the upper airway. OSA is characterized by repetitive pauses in breathing during sleep, despite the effort to breathe, and is usually associated with a reduction in blood oxygen saturation. These pauses in breathing, called "apneas" (literally, "without breath"), typically last 20 to 40 seconds.

Individuals suffering from OSA are rarely aware of having difficulty breathing, even upon awakening. It is recognized as a problem by others witnessing the individual during episodes or is suspected because of its effects on the body and/or conditions that is a consequence of a previous disease or injury (sequelae). OSA is commonly accompanied with snoring. Some use the term "obstructive sleep apnea syndrome" to refer to OSA which is associated with symptoms during the daytime. Symptoms may be present for years or even decades without identification, during which time the individual may become conditioned to the daytime sleepiness and fatigue associated with significant levels of sleep disturbance. Individuals who generally sleep alone are often unaware of the condition, without a regular bed-partner to notice and make them aware of their symptoms. If left unaddressed, these individuals can eventually suffer from non-reversible heart damage, increased blood pressure, and even stroke.

As the muscle tone of the body ordinarily relaxes during sleep, and the airway at the throat is composed of walls of soft tissue, which can collapse, it is not surprising that breathing can be obstructed during sleep. Although a very minor degree of OSA is considered to be within the bounds of normal sleep, many individuals can experience episodes of OSA at some point in life and a small percentage of people may suffer from chronic or severe OSA.

Continuous positive airway pressure (CPAP) is a treatment that uses mild air pressure to keep the airways open. CPAP typically is used by people who have breathing problems, such as sleep apnea. It can be difficult to maintain a desired degree of sealed interaction between the respiration or ventilation mask and the respiration path of wearer's or patients having various features including excessive or aggressive facial hair, anatomical facial anomalies, obese patients, and/or adentuless patients.

When preparing for the administration of anesthesia, an oxygen, respiration, or ventilation mask is placed on the patient's face to assure adequate or desired oxygenation. Maintaining a desired seal between the mask and the face of the patient will largely contribute to the degree of oxygenation communicated to a patient.

An anesthesia provider's maintenance of a patient airway largely affects the anesthesia process. Prior to induction of general anesthesia (procedure to produce loss of consciousness), patients are routinely pre oxygenated. This is accomplished by providing oxygen to the patient at a high flow rate through a tight fitting mask placed over the nose and/or mouth. This is usually done for several minutes. During induction, a patient is rendered unconscious with loss of protective airway reflexes and loss of breathing due to administered medications. It is during this time that the sealed interaction between the patients face and the mask by the anesthesia provider allows the desired and monitored ventilation of the patient. The presence of facial hair or other unusual facial anatomy detracts from the ability to obtain the desired adequate seal for oxygenation.

When a desired sealed interface is not achieved, the level of oxygen in the patient's blood drops as the oxygen escapes the respiration path at the interface between the mask and the patient. If unaddressed, such drops puts patient at risk of a cardiac event and may even lead to hypoxic injury. Patients with facial hair and unusual facial anatomy make it very difficult to achieve an adequate seal. Currently, when an airway problem exists as patients are anesthetized due to poor mask seal, extra personnel are employed and/or a variety of taping implemented to cover the face to achieve a desired tight, secure seal.

Currently, positive pressure noninvasive ventilation requires either both the hands of a single technician or multiple technicians responsible for maintain an adequate sealed interface between the mask and the patient and operation of the devices associated with generating the positive pressure respiration flows. Inadequate attention to the desired operation of the ventilation system and patient interface can result in poor patient oxygenation and the risks inherent thereto. It should be appreciated that such risks and the detriments associated therewith increase when inadequate attention is provided to the ventilation system associated with sedated patients in the hospital settings such as in the operating room, intensive care unit or patients that are otherwise incapable of providing an indication as to the poor oxygenation.

Recent years have shown an increase in patients diagnosed with obstructive sleep apnea (OSA). Treatment requires continuous positive airway pressure (CPAP) ventilation as they sleep. This is accomplished by a machine and delivered to the patient by mask. As positive pressure is applied, it keeps patients airway open and allows them to get a good night sleep without snoring or breath holding. If the patient has facial hair or facial anomalies they are not able to achieve an adequate seal resulting in the perception that that the CPAP machine is not helping or otherwise operating improperly. Such a perception leads many users to be considered noncompliant with prescribed treatments. Snoring and breath holding increases pressure in the vessels of the lungs and can lead to increased, pressure and ultimately enlargement of the heart. Not using CPAP, when prescribed, places patients at risks of developing heart conditions caused by obstruction of the airway and periods of not breathing (apnea). As a result these patients suffer lethargy during the day, reduced exercise tolerance, enlarged heart leading to reduced percentage of heart muscle function, and weight gain.

Currently ventilation or respiration masks commonly include a plastic cushion or pillow that rests upon the skin of the user. If a small leak develops in such mask systems, the pressure drops. The contact between the cushion or pillow and the skin of the user as well as the leakage is commonly detrimental to the patient and can lead to sores, skin ulcers that are very difficult to heal when repetitive pressure is applied to the affected skin, eruptions, and dry eye conditions if the leak is directed toward the ocular anatomy of the wearer. Also if a leak is present, the auto-adjusting CPAP machines increase the pressure to keep the airway open which can lead to gastric distention and painful abdominal bloating, belching, and increase in gastroesophageal reflux leading to discontinuation of the use of the CPAP.

Currently, patients undergoing eye surgery also have to discontinue the use of the CPAP as any small leak could lead to conjunctivitis and/or infection of the eye.

Management of the respiratory distress in neonates and infants is also extremely important to their survival. CPAP is considered a simple and effective therapy for respiratory distress of the neonates. The correct application of CPAP can decrease the work of breathing, prevent airway collapse, and reduce oxygen requirements as high oxygen concentration can be detrimental to addressing the health concerns of infants undergoing such treatment.

Therefore, there is a need for a seal device and methods of improving respiration assistance and ventilation practices that provides a generally, but not necessarily absolute, sealed interaction between the perimeter edge of the mask and anatomy or features of wearers having various facial features including facial hair as well as other anatomical abnormalities or unique structures. There is also a need for a ventilation/respiration assistance device that mitigates the detrimental consequences associated with extended periods of ventilation or exposure of the epidermis of the user to the respiration flow and/or interaction with the perimeter edge of masks associated with such activities.

SUMMARY OF THE INVENTION

The present invention discloses methods and devices for overcoming one or more of the drawbacks discussed above. One aspect of the invention discloses a seal device or gasket assembly that is usable with respiration or ventilation mask systems and that is preferably at least one of adhesive or deformable. The seal device is disposed between a mask and the wearer, adhering to the face, and/or the face and mask and reduces the escape of respiration gases between the perimeter edge interfaces of the mask with the anatomy of the wearer. The device also reduces exposure of epidermis located within the perimeter edge of the mask and between the mask and the wearer to the respiration gas flows. The mask system is particularly useful for improving communication of the respiration gases for those wearers having facial hair, abnormal dontia, following eye surgery, neonates and/or other abnormal facial features and/or facial asymmetry such as associated with partial facial paralysis commonly associated with stroke, paralysis and/or Bells Palsy.

Another aspect that is usable or combinable with one of the more of the above features or aspects discloses a method of forming a device for improving wearer ventilation. The method includes providing a generally planar flexible body defined by a first lateral side and a second lateral side that extend on opposite sides of the seal body between a perimeter edge of the body. A removable backer material is engaged with an adhesive disposed along the first lateral side of the generally planar flexible body and the adhesive is selected to be removably securable to an epidermis of a wearer. The generally planar flexible body is shaped to cooperate with the epidermis of the wearer proximate a respiration flow passage; be it the mouth, nasal passage, or both; so that the generally planar flexible body is disposed between the wearer and a perimeter edge of a mask.

Another aspect of the invention that is usable or combinable with one or more of the above features or aspects discloses a method of ventilating a patient that includes adhering a first side of a seal device to a face of a wearer so that the first side of the seal device adheres to the epidermis of the wearer in a manner wherein the seal device substantially surrounds a respiration flow passage of the wearer. A mask can be engaged with a second side of the seal device that is opposite the first side so that the seal device isolates a majority of the mask from contact with the epidermis of the wearer and isolates that portion of the epidermis within the perimeter of the mask from exposure to the gases and/or moisture associated with the respiration flow.

A further aspect that is usable of combinable with one or more of the above features and/or aspects discloses a device for improving a sealed interface between a respiration mask and a face of a wearer. The device includes a seal body having a first side that faces toward facial anatomy of a wearer. An adhesive layer that adheres to an epidermis of a user is associated with the first side of the seal body. A second side of the seal body that is opposite the first side is configured to engage a perimeter edge of a mask. A backer is attached to the first side of the seal body and removably cooperates with the adhesive layer such that removal of the backer exposes the adhesive for securing the adhesive layer to the epidermis of the user proximate a respiration path opening of the user.

These and various other features, aspects, embodiments and alternatives of the present invention will be made apparent from the following detailed description taken together with the accompanying drawings. It should be understood, however, that the detailed description and specific examples, while indicating preferred embodiments of the invention, are given by way of illustration and not limitation. Many changes and modifications can be made within the scope of the present invention without departing from the spirit thereof, and the invention includes all such modifications.

BRIEF DESCRIPTION OF THE DRAWINGS

Preferred exemplary embodiments of the invention are illustrated in the accompanying drawings, in which like reference numerals represent like parts throughout, and in which.

DETAILED DESCRIPTION OF THE PREFERRED EMBODIMENTS

Figure 1:
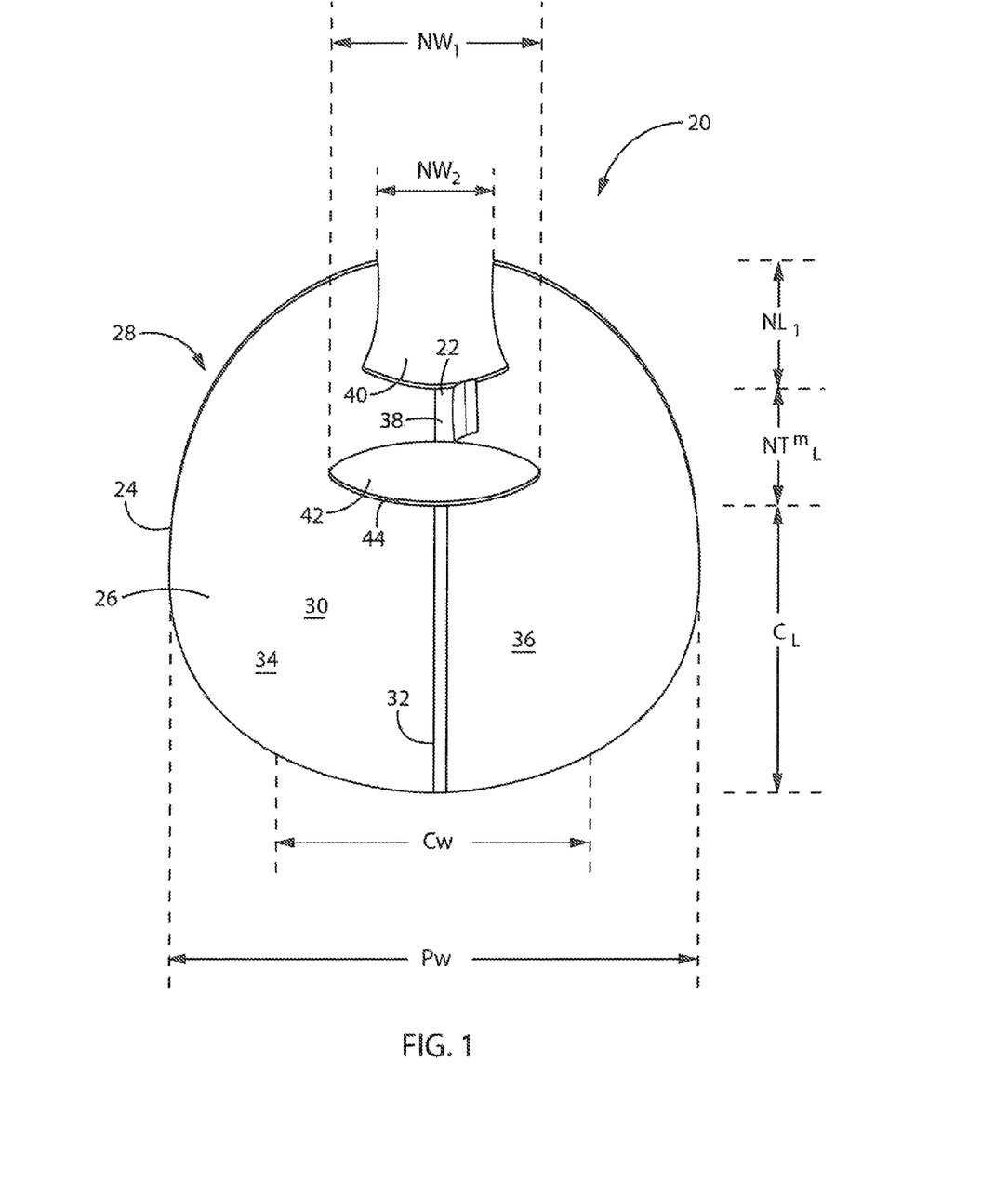
FIG. 1 is a perspective view of a seal device according to one aspect of the invention with a backer partially removed from a patient or wearer facing side of the seal device.
Figure 2:
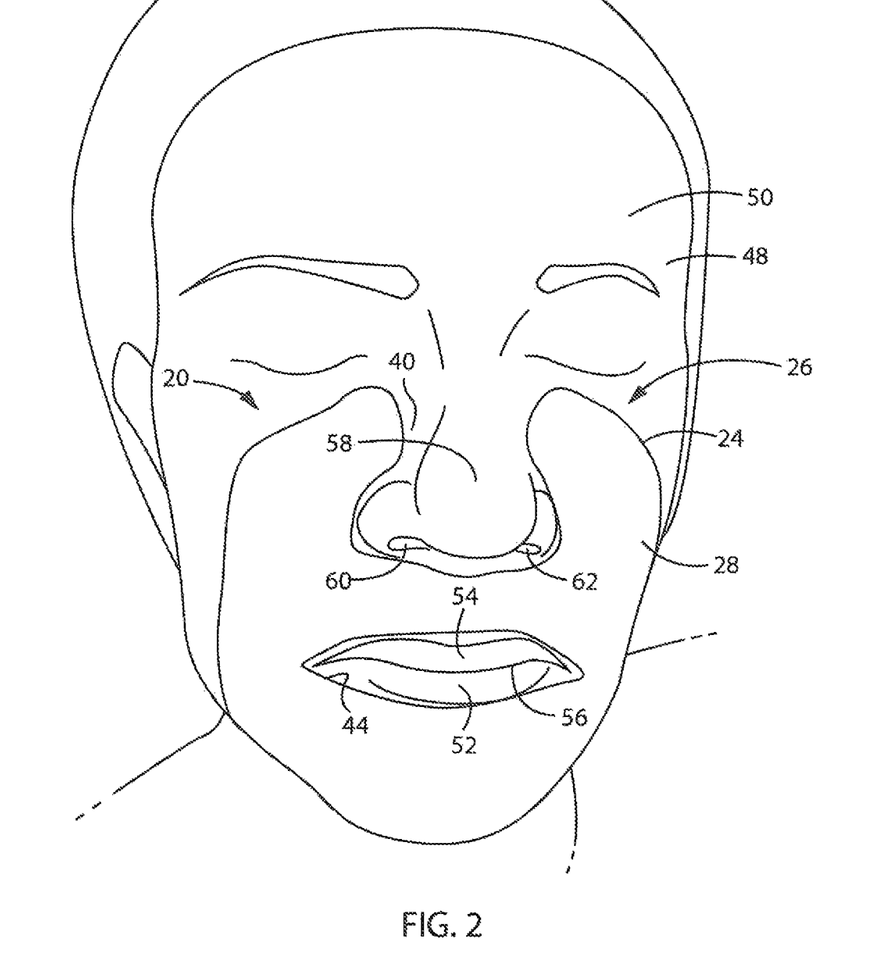
FIG. 2 is a front elevation view of the seal device shown in FIG. 1 secured to a face of a wearer.

The present invention contemplates various embodiments for generating a desired degree of "sealed" interaction between the mouth and/or nasal area of a wearer or patient and a respiration or ventilation mask constructed to cooperated with only the face of the wearer as compared to more robust respiration hoods or the like. FIGS. 1 and 2 show a gasket or seal device 20 according to one aspect of the present invention. In one aspect of the invention, seal device 20 is defined by a body 22 formed of a film like material.

Body 22 is generally defined by a perimeter edge 24 that bounds a first or patient or wearer side 26 and a second or mask facing side 28 of body 22. A backing material 30 is removably adhered to wearer side 26 such that removal of backing material 30 selectively exposes an adhesive material or layer disposed therebehind. Mask side 28 of body 22 can also include an adhesive material or layer and a selectively removable backing material associated therewith. As disclosed further below, the adhesive layer associated with wearer side 26 of body 22 is selectively adhereable to the epidermis, facial hair, or auxiliary structures without detrimentally affecting the integrity of the underlying structure. In a preferred embodiment, backing material 30 includes a seam edge 32 that defines a first portion 34 and a second portion 36 of backing material 30. Seam edge 32 allows respective packing portions 34, 36 to be sequentially removed from body 22 to selectively expose respective portions of an adhesive surface or layer 38 disposed therebehind. Although shown as being oriented along the medial line of device 20, it is appreciated that seam edge 32 could be oriented at any respective location of device 20, need not be linear, and could be oriented along a portion of body 20 so as to generally align with a respective anatomical feature of a user during application of the device.

Body 22 includes a cut out 40 associated with perimeter edge 24. Cut out 40 is shaped to cooperate with the nasal features of a wearer. Although shown as terminating short of the bridge of the nose, as disclosed further below, it is appreciated that cutout 40 could be shaped as an opening to generally circumscribe the nose of the wearer. Body 20 includes an opening 42 defined by an edge 44 located within outer perimeter edge 24. Opening 42 is sized to cooperate with the mouth of a wearer such that body 22 does not interfere with the respiration path associated with the user's mouth or the user's nasal passages. It is further appreciated that cutout 40 and opening 42 could be provided in various sizes and shapes to accommodate use of device 20 with user's having different facial features, detriments, or sizes; such as adult, adolescent, neonate, and infant sizes. It is further appreciated that the size of device 20, and the cutouts and or openings associated therewith, could further be categorized based on a gender as well as the age of the intended user.

As shown in FIG. 2, removal of backing material 30 from wearer side 26 allows seal device 20 to be secured to a face 48 of a wearer 50 such that edge 44 cooperates with face 48 proximate the lips 52, 54 of wearer 50 and does not overlay the mouth opening 56 of wearer 50 and cutout 40 partially circumscribes a nose 58 of wearer 50 such that body 22 does not overlie nostrils 60, 62 of wearer 50 but is disposed in close proximity thereto. As disclosed further below, when adhered to face 48 of wearer 50, mask side 28 of body 22 is oriented to cooperate with a patient or user facing side of a respiration or ventilation mask. It is appreciated that the close proximity of device 20 to the mouth and nasal openings of wearer 50 as well as the extension of device 20 about the general face area or wearer 50 allows use of device 20 with respiration or ventilation masks having a variety of sizes, shapes, and constructions.

As alluded to above, mask side 28 of device 20 may also include an adhesive surface or layer for selectively removably cooperating with a mask disposed over face 48 of wearer 50. Body 22 is preferably adhered to face 48 in close proximity to lips 52, 54 and nostrils 60, 62 thereby reducing the portion of the epidermis of user 50 that is located within the perimeter of a respiration mask from exposure to the gases and/or moisture associated with the respiration or ventilation gas flows. Such a consideration reduces the potential for the generation of sores or other irritations to the skin commonly attributable to extended periods of ventilation. Tegaderm® material currently available from 3M Company has been shown through testing to be one such suitable pliable film material.

Figure 3:
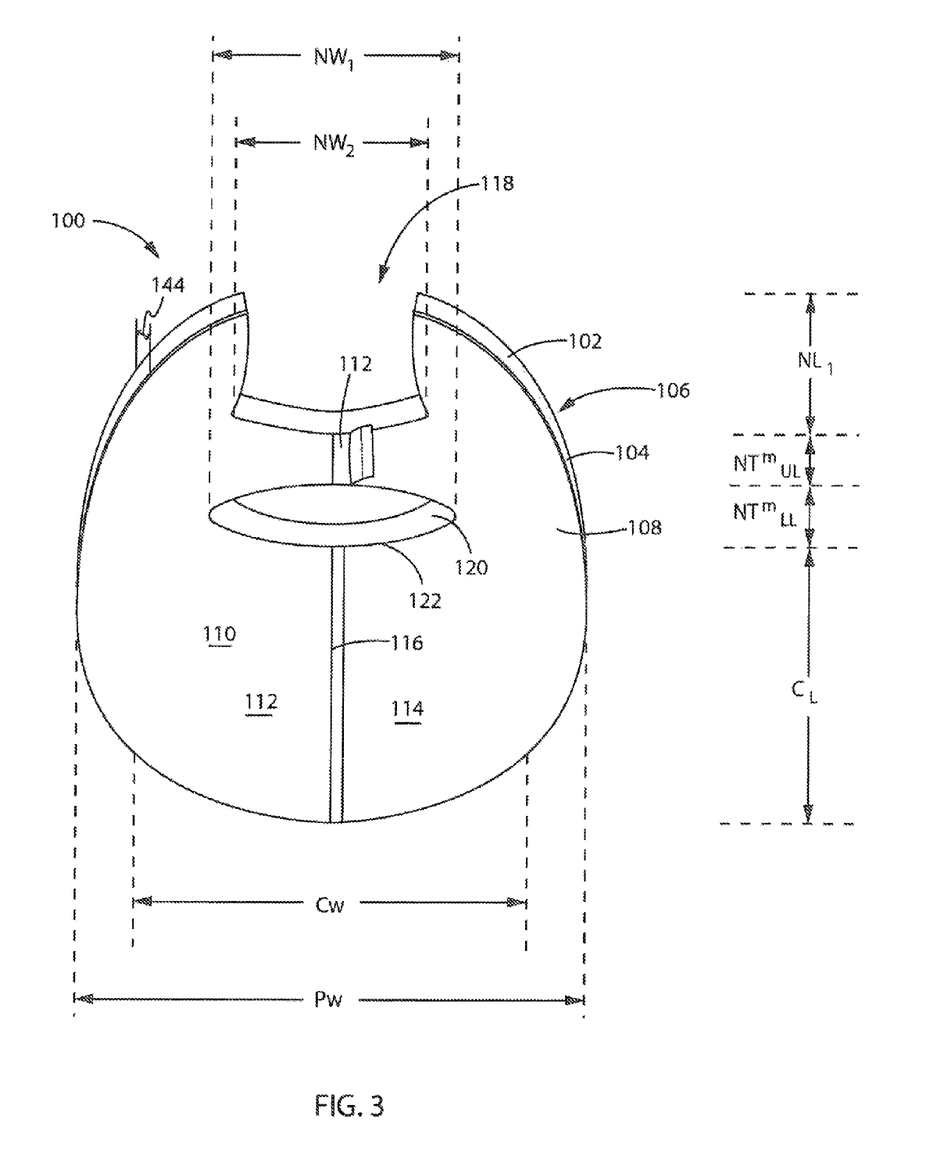
FIG. 3 is a view similar to FIG. 1 of a seal device according to another aspect of the invention.
Figure 4:
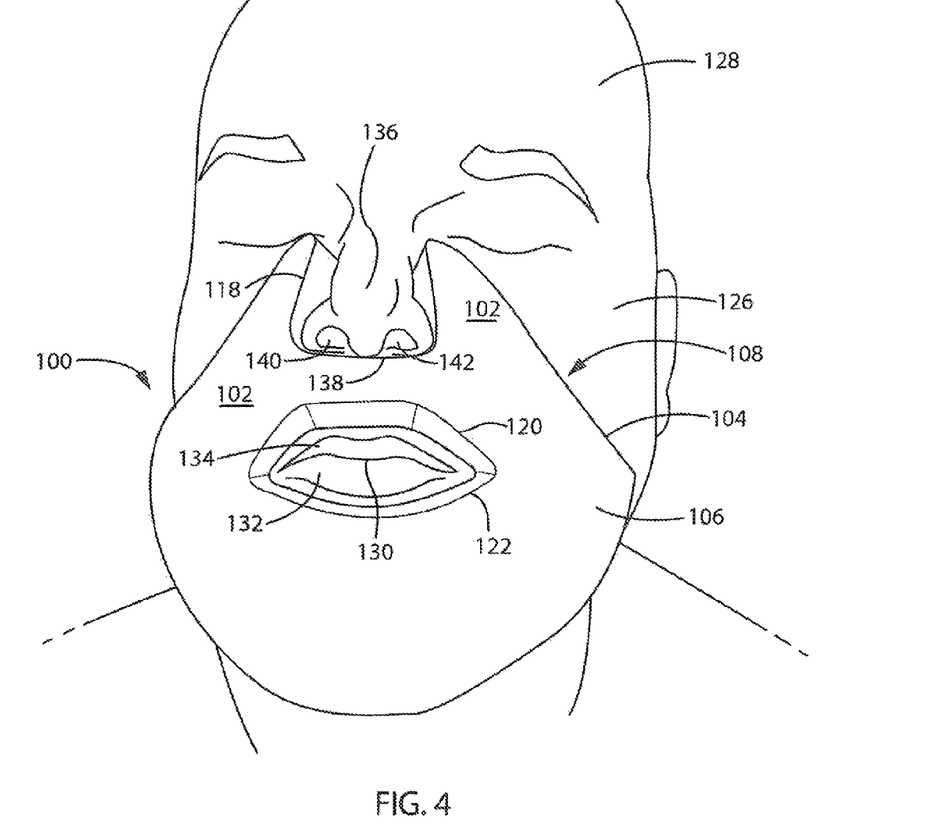
FIG. 4 is a view similar to FIG. 2 of the seal device shown in FIG. 3.

FIGS. 3 and 4 show a seal device 100 according to another aspect of the invention. Seal device 100 includes a body 102 defined by a perimeter edge 104 that circumscribes a mask side 106 and a wearer side 108. A backer material 110 removably cooperates with an adhesive surface or layer 112 associated with wearer side 108. In a preferred aspect, backer material 110 includes a first portion 112 and a second portion 114 that are separated by a seam edge 116 to allow selective exposure of respective portions of adhesive layer 112 it is appreciated that seam edge 116 could be provided in virtually any position relative to body 102 as may be desired to facilitate placement and/or convenient removal of backer material 110 from body 102. It is further appreciated that the functionality of seam edge 116 could be provided as one or more pull tabs with no adhesive feature but otherwise configured to be conveniently able to be gripped by a user or technician intending to apply device 100 to a user in a desired position without required interaction with an exposed adhesive surface associated with body 102.

Like body 22, body 102 includes a cut out 118 associated with perimeter edge 104 that is shaped to accommodate the nasal features of a wearer. An opening 120 is formed through seal device 100 and is offset from nasal cut out 118 and defined by an edge 122 shaped to closely cooperate with the mouth of a wearer. Like device 20, it is appreciated that the shape and site of cutout 118 and/or opening 120 of device 100 may each be manipulated during application of device 100 to achieve a desired interaction of the device with the underlying anatomy or facial features of a respective user.

Referring to FIG. 4, when backer material 110 is removed from wearer side 108 of body 102, seal device 100 may be removably adhered to a face 126 of a wearer 128 such that opening 120 does not obscure a mouth 130 and edge 122 is secured proximate lips 132, 134 of wearer 128. Cut out 118 generally circumscribes a portion of nose 136 of wearer 128 such that a lower edge 138 of body 102 is adhered proximate nostrils 140, 142 of wearer 128. As alluded to above, mask side 106 of body 102 may also include an adhesive layer and corresponding backing material to removably cooperate with a mask disposed over face 126 of wearer 128.

It should be appreciated that whereas body 22 of seal device 20 is formed of a film like material, and has fairly thin thickness, body 102 of seal device 100 is formed of a foam type material and has a thickness, indicated by arrow 144 (FIG. 3) that is greater than a thickness of seal device 20. The foam like material of body 102 of seal device 100 is selected so as to be impermeable to gases but deformable to accommodate greater deviations associated with providing a sealed interaction between a mask associated with mask side 106 of seal device 100 and the facial features associated with the respective wearer 128. That is, seal device 100 is beneficial if the wearer or patient has facial irregularities such as scars, dentures that have been removed, or facial asymmetry. The foam seal device is also adhesively applied to the face of the wearer and conforms to the patients face and forms a seal with the mask that is less likely to have leakage associated therewith. The various materials associated with the various seal devices disclosed herein accommodate positive pressure ventilation associated with use of any of the respective seal devices disclosed herein.

Figure 5:
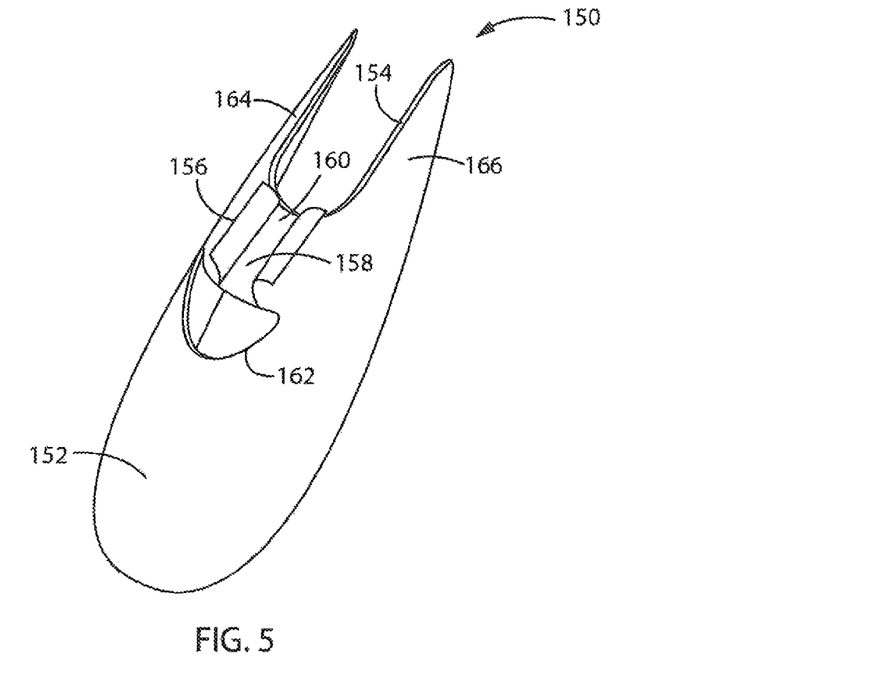
FIG. 5 is a view similar to FIG. 1 of a seal device according to another aspect of the invention.
Figure 6:
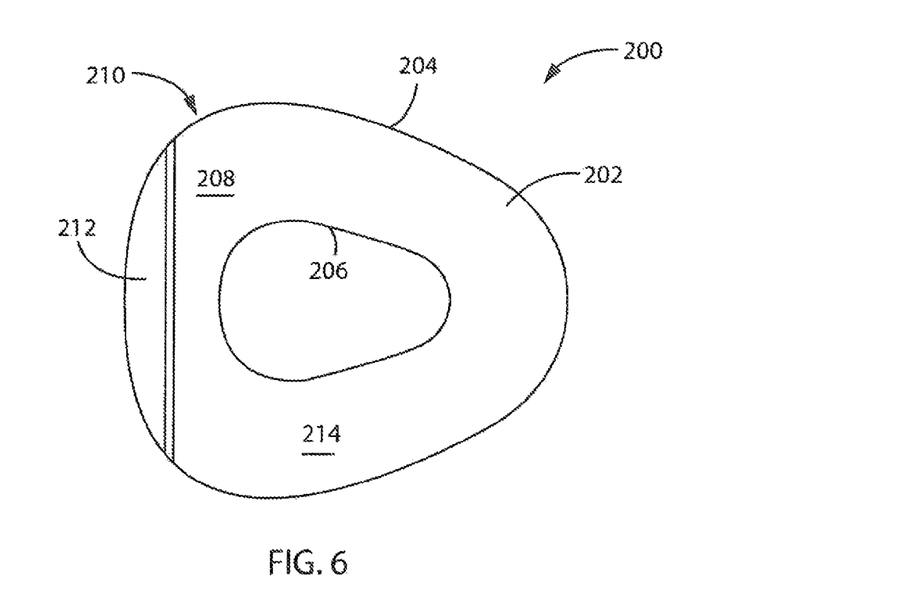
FIG. 6 is a view similar to FIG. 5 of a seal device according to another aspect of the invention.
Figure 7:
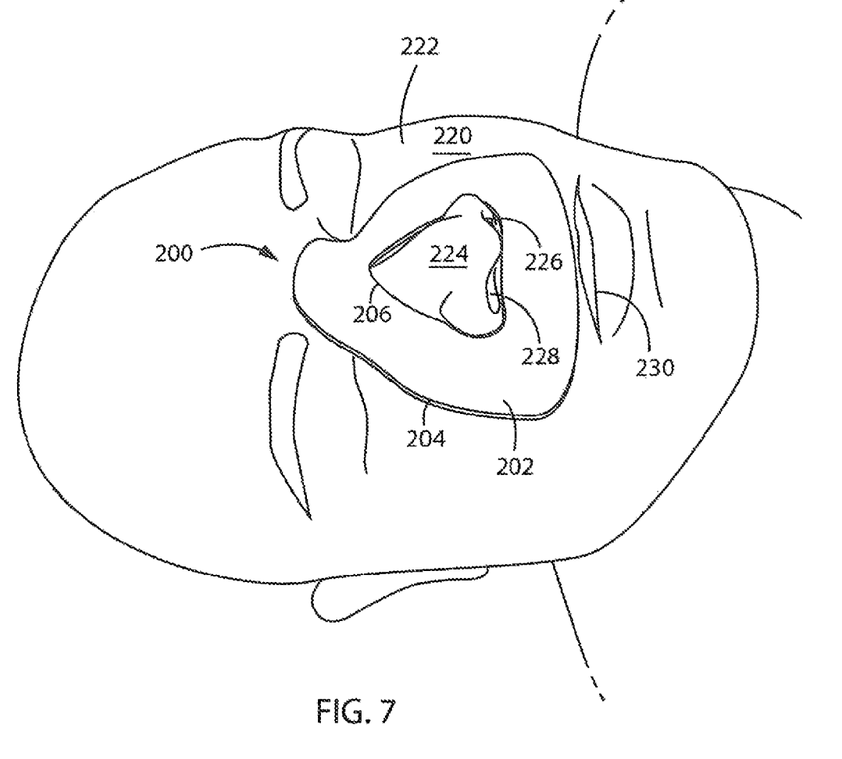
FIG. 7 is a view similar to FIG. 2 of the seal device shown in FIG. 6.

FIGS. 5-7 show respective seal devices 150, 200 according to further aspects of the present invention. Seal device 150 is defined by a generally planar shaped but flexible body 152 that is generally defined by a perimeter edge 154. The shape of body 152 is generally similar to the shape of seal devices 20, 100. Seal device 150 is shown folded partially over itself so as to improve the simplicity associated with the separation between a backer material 156 and an adhesive surface or layer 158 associated with a patient or wearer side 160 of seal device 150. It should be appreciated that backer material 156 is provided in a configuration wherein an optional seam edge 162 is provided between a first portion 164 and a second portion 166 of backer material 156 so as to facilitate the manual separation between the respective portions of the backer material and the adhesive surface of the body for application of seal device 150. It should further be appreciated that such a configuration allows the respective seal device to be applied without repeated contact with the exposed adhesive surface or layer associated with the user facing side of seal device 150.

It should further be appreciated that each of seal devices 20, 100, 150 are each configured for usage with either of a nasal or a full face ventilation or respiration mask. As used herein, a nasal respiration mask is commonly understood to cooperate with primarily the nose and nasal features of the wearer whereas a full face respiration mask can be provided in configurations wherein the respiration mask cooperates with the mouth or mouth and nasal respiration passages. It is appreciated that each of the various seal devices disclosed herein can be provided in configurations usable for use with one or both of mouth and nasal respiration passages. It is further understood that a seal device provided for use with a full face respiration mask can be utilized for use with nose only respiration masks for those applications wherein use of such respiration masks provides adequate respiration or ventilation performance.

Referring to FIGS. 6 and 7, seal device 200 includes a body 202 whose shape is defined by perimeter edge 204 and an edge 206 that is circumferentially bounded by body 202 and outer perimeter edge 204. Like seal devices 20, 100, 150, seal device 200 includes a user facing side 208 and a mask facing side 210. A removable backing material that includes an option first portion 212 and second portion 214 is preferably adhered to an adhesive associated with patient facing side 208 of body 202. Backing material 212, 214 removably cooperates with body 202 to expose the adhesive surface or layer disposed therebehind. Once exposed, body 202 can be selectively secured to a face 220 of the user 222 such that body 202 circumscribes a nose 224 and the nasal passages 226, 228 associated therewith. Body 202 does not otherwise interfere with the mouth respiration passage 230 of user 222.

As disclosed further below, seal device 200 is configured to cooperate with a nasal respiration mask. Seal device 200 prevents direct contact of the user facing side of the respiration mask with the epidermis of the user 222 and is constructed to reduce the surface area of the epidermis of the user that is exposed to the respiration flow path and the gases associated with. Unlike seal device 20, which is formed of a film material, and seal device 100, which is formed of a foam material, seal devices 150, 200 are formed of a hydrocolloid material as disclosed further below.

Figure 8:
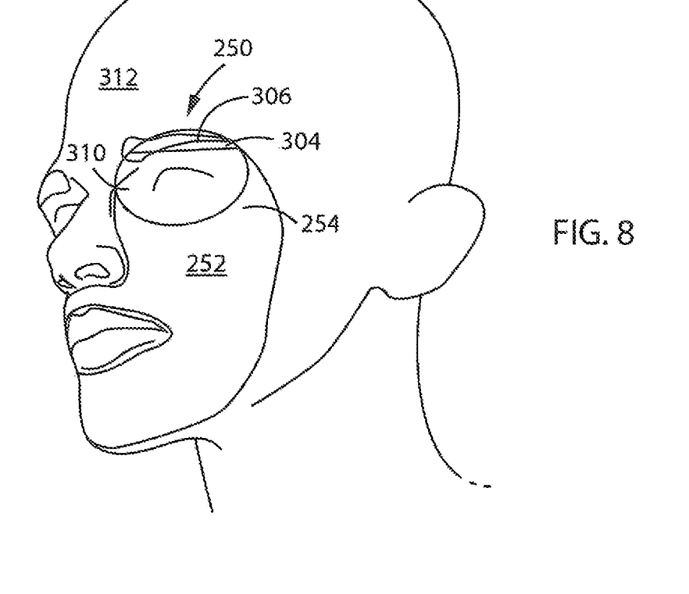
FIG. 8 is a perspective view of a seal device according to another aspect of the invention secured to a face of a wearer.
Figure 9:
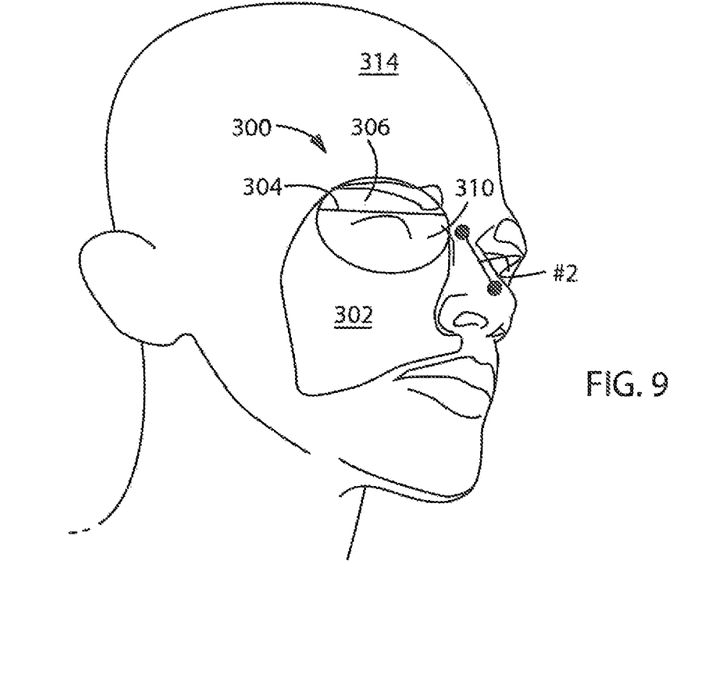
FIG. 9 is a view similar to FIG. 8 and shows a seal device according to another aspect of the invention secured to the face of a wearer.

FIGS. 8 and 9 show seal devices 250, 300 according to alternate aspects of the present invention. Seal device 250 is defined by a body 252 that is formed of a film material similar to seal device 100 whereas seal device 300 is defined by a body 302 formed of a hydrocolloid material similar to seal devices 150, 200. Unlike seal devices 20, 100, 150, 200, seal devices 250, 300 each include an elongated portion or tab 304 that at least partially cooperates with a non-respiration related anatomical feature and/or an auxiliary medical device 306 that is not otherwise associated with the patient respiration performance.

As shown in FIGS. 8 and 9, device 306 is shown as a protective structure associated with covering an eye socket 310 of the user 312, 314. The tab 306 associated with the respective body 252, 302 of respective seal devices 250, 300 extends over at least a portion of the non-respiration anatomy or protective structure or device 306 and reduces exposure of anatomy disposed therebehind to the respiration or ventilation gas flows. It is further appreciated that seal devices formed of other materials, such as foam seal device 100, could include similar such tab features to prevent exposure of compromised or non-respiration related anatomy to respiration gas flows that may escape between the cooperation of the mask and the anatomy of the user and/or the seal device associated therewith.

Figure 10:
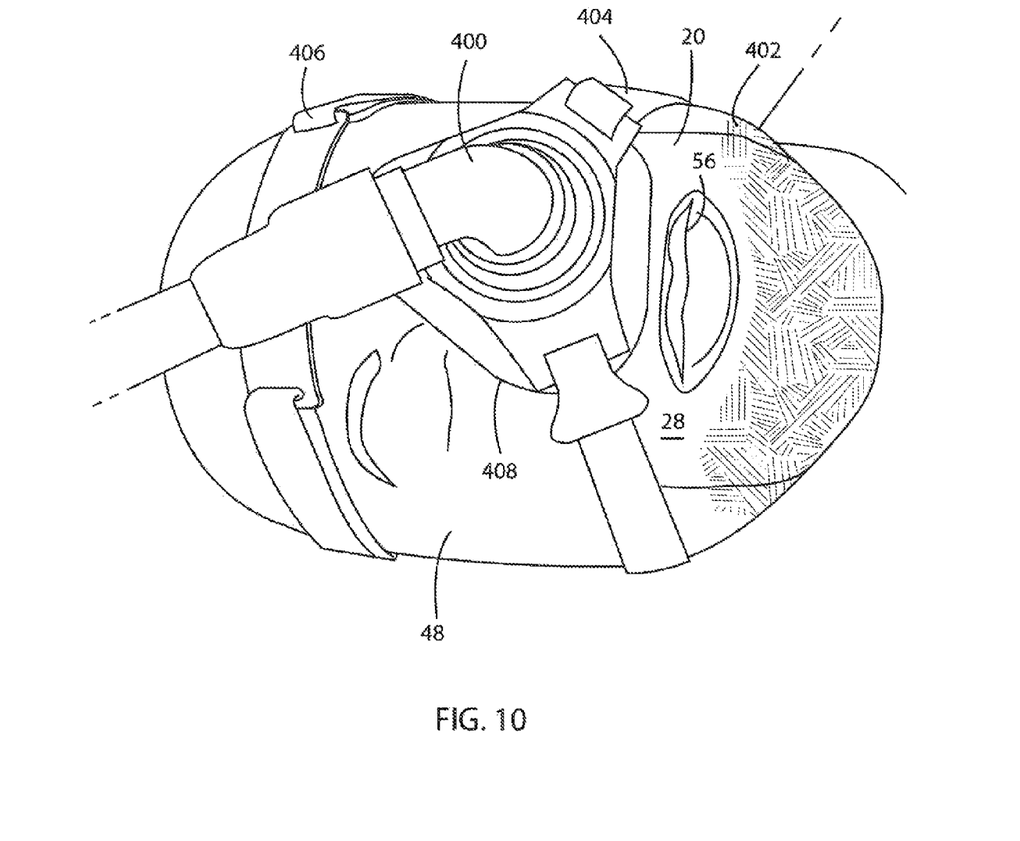
FIG. 10 shows wearer associated with a respiration or ventilation mask and having a seal device like that shown in FIG. 2 disposed between the face of the wearer and the mask.

Referring to FIG. 10, seal device 20 is shown engaged the face of the wearer 48 and with a respiration mask 400 associated therewith. Seal device 20 is secured to the epidermis or facial hair of the user 48 and overlays facial features such as facial hair 402, reduced dontia, or patients suffering from abnormal dontia, and/or other abnormal facial features and facial asymmetry such as those associated with stroke effects, partial facial paralysis, or Bells Palsy. Following eye surgery or for those patients susceptible to ocular infection, a respective seal device 20, 100, 150, 200, 250, 300 can be configured to include a tab configured to overlie at least a portion of an eye socket or protective appliance associated therewith to isolate the ocular features and anatomy from exposure to the respiration and/or ventilation flows. Mask 400 includes one or more optional straps 404, 406 that maintain a secure contact engagement between a perimeter edge 408 of mask 400 and seal device 20. For those embodiments wherein the mask facing side of the respective sealing device includes an adhesive surface or layer, the user facing side of mask 400 can be selectively sealed to the respective sealing device via the interaction of the user facing side of mask 400 with the respective seal device. Seal device 20 extends beyond the user facing surface associated with mask 400 associated with the enclosed respiration flow passage thereby reducing exposure of that portion of the users epidermis that would be exposed to the respiration flow gases without use of seal device 20. Seal devices 20, 100, 150, 250, 300 also extend radially beyond the outer radial edge associated with many commercially available respective respiration masks such that each of seal devices 20, 100, 150, 200, 250, 300 can be utilized with respiration or ventilation masks having various shapes and sizes.

Although shown as a nasal respiration mask, it is appreciated that the seal device 20 shown in FIG. 10 allows respiration or ventilation of a user or patient with either of a nasal respiration mask 400, as shown in FIG. 10, or via a mask configured to generally overlie both the mouth 56 and the nasal respiration passages depending upon the availability of a respective respiration mask and/or the degree of respiration or ventilation required. It is further appreciated that each of seal devices 20, 150, 250, 300 can also be applied to a wearer in a manner wherein portions of the respective seal device are adhered to one another in an overlapping manner to limit the extension of the respective seal device to those areas proximate the interaction of the intended mask with the underlying anatomy of a wearer.

Each of respiration seal devices 20, 100, 150, 200, 250, 300 provide a respiration seal device wherein one side of the respective device selectively removably cooperates with the epidermis or facial tissue, anatomy, or facial hair of the wearer and the other side cooperates with a perimeter edge of a respiration mask. Each respective seal device includes a removable covering or backer material that is associated with an adhesive that is configured to selectively removably adhere to skin tissue or facial hair. Preferably, the adhesive materials are selected to cooperate with the respective structures in a manner that is non-detrimental to the underlying features or dermis and is reusable for multiple ventilation episodes. A respiration mask can be placed over the film, foam, or hydrocolloid material associated with the respective seal device and securely engaged therewith or otherwise secured to the patient to substantially seal the perimeter edge of the mask with the respective seal device. Preferably, the adhesive associated with the patient facing side of the seal device adheres to hair and epidermis and is preferably robust enough to accommodate single or multiple uses of the seal device with a single patient and/or repeated application of respiration masks.

Each of seal devices 20, 100, 150, 200, 250, 300 is formed by a deformable or pliable film, foam, or hydrocolloid material that can be configured to accommodate abnormal and non-clean shaven facial features. Preferably, at least one or both sides of the respective seal device include an adhesive surface or layer that can selectively cooperate with facial hair or anatomy or a wearer as disclosed above. The seal preferably includes a removable backing configured to protect the integrity of the adhesive layer until utilization of the seal is desired. Such a seal is also configured to accommodate a desired degree of sealed interaction between a respiration or ventilation mask and the face of the user or patient with facial hair and facial anatomical anomalies including adentuless patient. The elongated interfere of the respective seal device with the underlying structure of the wearer allows a respiration mask to cooperate with the respective seal in various positions and in a manner that mitigates leakage of the respiration gases between the interface of the respective seal device and the underlying patient and the interface of the respective mask and the respective seal device.

It is further appreciated that each of seal devices 20, 100, 150, 200, 250, 300 can be provided in various sizes to accommodate different respective patients. It is appreciated that the various dimensions associated with the respective cutouts and/or openings associated with the respiration flow passages of the wearer can be configured to accommodate different ranges in sizes associated with the underlying user. It is further appreciated that, the various variables associated with the dimensions of the respective seal devices correlate to the association of various anatomical features of a wearer to an outside perimeter associated with the respective seal and a perimeter shape of a respiration or ventilation mask intended to be used therewith in accordance with the features and size of different respective users so as to improve the applicability of seals 20, 100, 150, 200, 250, 300 with little to no point of use modification to the same.

For users intended to individualize a respective seal device, the user first measures their discrete nostril to nostril to nostril distance and tip to bridge of nose distance. The dimensions can then be coordinated to a respective seal device such that the respective seal device can include a cutout or opening associated with the nasal features of the user and correlate thereto to provide a sealed interaction with the features of a discrete user. Alternatively, the respective seal device could be provided with a horizontal line and a median line. The width at the lower end of the nose could be indicated on the horizontal line so that the median of the width is coincident with the intersection of the median and horizontal lines. The length of the nose could be indicted on the medial line so that the lower end of the length line is coincident with the intersection of the lateral line and the median line and the upper end of the length line is disposed above the horizontal line. Connecting the upper end location associated with the medial line and the outer lateral end measurement indications associated with the horizontal line and cutting out the portion of the seal device between the out pitched lines and the horizontal lines allows customization of the seal device for cooperation with the nasal features and anatomical structure of the discrete user.

Each of seals 20, 100, 150, 200, 250, 300 enable wearers, care givers, anesthesia providers, or any emergency caregiver, to mask-ventilate a patient using one hand while maintaining a clear view of the patient's face and airway. The airway can be taped directly over the film. As disclosed above, it is further appreciated that one or more of seal devices 20, 100, 150, 200, 250, 300 can be configured for use with patients who need to wear an eye shield in cases such as recent eye surgery and/or eye injury. A plastic eye shield is applied over the eye and the respective seal is applied over the facial hair and incorporating the bottom of the eye shield. Application of a respiration or ventilation mask over the film creates a seal which prevents respiration gases from leaking under the shield. It is further envisioned that seal 80 could extend on one side to go over the patch on a side of the eye patch and will cover up to the middle of the eye patch to allow light to filter through one or more holes associated with implementation of the eye patch.

The seal device according to one or more of the aspects disclosed herein is comfortable to wear as well as easy to implement and use with various respiration and ventilation masks so as to improve patient compliance with prescribed treatments and therefore reducing the health risks and improving quality of life. The various seal devices disclosed herein provide users with a desired seal performance associated with use of ventilation and respiration masks in a manner that does not require alteration of the user's appearance thereby increasing compliance for instances of self-applied respiration masks. The present invention also substantially reduces instances of initial difficulties of mask oxygenation so as to be manageable by a single user or technician. The inter face-to-mask seal devices of the present invention improve the ability of health care providers as well as self-applied mask wearers to maintain a desired degree of sealed interaction between the mask and the facial anatomy and features. Preferably, each of the seal devices disclosed herein provide an absolutely occlusive seal between a patient's face and mask airways used for patient pre oxygenation prior to the administration of anesthesia and patients with diagnosis obstructive sleep apnea (OSA) and secure mask/face contact to provide a desired leak reduced patient ventilation regardless of the reason associated with usage of the underlying respiration mask.

The ease of use of the interface seal makes it easily applied by anesthesia providers, paramedics, emergency room doctors, respiratory therapists, and users. It can be used in various applications and environments including in home, hospital, ambulances, emergency rooms and intensive care units. It is envisioned that the sealed respiration system in accordance with the various aspects of the present invention can be used by emergency medical technicians (EMT's), ambulance, flight for life, hospitals, emergency rooms, other medical technicians, home care, and patients with varying degrees of cognitive and/or motive infirmities. The respiration devices according to the present invention allow treatment of patients with facial hair growth to create a seal between the mask and their face.

The proposed mask and seal system also improves patient compliance in the use of CPAP machines in patients who otherwise could not achieve an adequate seal. The proposed assembly also reduces complications caused when CPAP machines are not used in patients diagnosed with sleep apnea. The proposed respiration seal device systems also reduce the number of personnel associated with securing a sealed delivery of oxygen to a patient. The proposed respiration mask also reduces other undesired consequences that can be caused by the inability to obtain an adequate seal, such as lung disease, heart disease, and reduction in energy or ability to stay active during use of such respiration assisting appliances. Additionally, each of the seal devices disclosed herein is configured to accommodate humidification of respiration cases thereby avoiding dehydration of the mucus membranes associated with the respiration flow paths without developing pressure sores or tissue ulcers even when provided during positive pressure respiration assistance treatments.

Although the best mode contemplated by the inventors of carrying out the present invention is disclosed above, practice of the present invention is not limited thereto. It will be manifest that various additions, modifications and rearrangements of the aspects and features of the present invention may be made in addition to those described above without deviating from the spirit and scope of the underlying inventive concept. The scope of some of these changes is discussed above. The scope of other changes to the described embodiments that fall within the present invention but that are not specifically discussed above will become apparent from the appended claims and other attachments.

We claim:

1. A method of forming a device for improving wearer ventilation, the method comprising:
   providing a generally planar flexible body defined by a first lateral side and a second lateral side that extend on opposite sides of the generally planar flexible body between a perimeter edge of the generally planar flexible body and includes a removable backer material that is engaged with an adhesive disposed along the first lateral side of the generally planar flexible body, wherein the adhesive is removably securable to an epidermis of a wearer; and
   shaping the generally planar flexible body to cooperate with the epidermis of the wearer proximate a respiration flow passage so that the generally planar flexible body continuously circumscribes no more than one discrete respiration flow passage and is disposed between the wearer and a perimeter edge of a mask and isolates as least one non-respiration related anatomical feature from a flow associated with use of the mask and shaping the generally planar flexible body to define at least one tab that extends at an upper portion the body, and overlaps at least a portion of a wearer's eye socket.

2. The method of claim 1 further comprising splitting the removable backer material so that respective portions of the adhesive can be selectively exposed.

3. The method of claim 1 wherein the generally planar flexible body is further defined as one of a film material, a hydrocolloid material, and a foam material.

4. The method of claim 1 further comprising providing another removable backer that is engaged with another adhesive disposed on the second lateral side of the generally planar flexible body wherein the another adhesive is selectively removably securable to a perimeter edge of a mask.

5. The method of claim 1 wherein shaping the generally planar flexible body is further defined as providing only one of a nasal flow passage and an oral flow passage through the generally planar flexible body.

6. The method of claim 5 wherein when the nasal flow passage is provided, the nasal flow passage is circumferentially bounded by a continuous edge of the generally planar flexible body.

7. The method of claim 1 further comprising using the device with the same wearer for multiple ventilation periods wherein each ventilation period is defined by a respective application and respective removal of the generally planar flexible body from the epidermis of the same wearer.

8. A method of ventilating a patient, the method comprising:
adhering a first side of a seal device to a face of a wearer so that the first side of the seal device adheres to the epidermis of the wearer in a manner wherein the seal device circumferentially surrounds a single respiration flow passage of the wearer;
engaging a mask with a second side of the seal device that is opposite the first side so that the seal device isolates a majority of the mask from contact with the epidermis of the wearer and the seal device isolates anatomy that is inboard of an edge of the mask from exposure to respiration flow; and
shaping the seal device to overlap at least a portion of at least one eye socket of the wearer.

9. The method of claim 8 further comprising shaping the seal device to extend circumferentially about the respiration flow path such that the seal device isolates the epidermis of the wearer that is between a perimeter surface of the mask and an opening associated with the respiration flow passage from exposure to the respiration gases.

10. The method of claim 9 further comprising repeatedly adhering and removing the first side of the seal device from the face of the same wearer.

11. The method of claim 8 further comprising shaping the seal device to cooperate with at least one of a mouth and a nasal passage of the wearer.

12. The method of claim 8 wherein adhering the first side of the seal device to the face of the wearer further comprises removing a backer material from first side of the seal device.

13. The method of claim 12 further comprising removing a backing material from the second side of the seal device prior to engaging the mask with the second side of the seal device.

14. The method of claim 8 wherein adhering a first side of the seal device to the face of a wearer further comprises selecting a seal device formed from one of a film material, a hydrocolloid material, and a foam material and selecting a shape and a size of the selected seal device associated with at least one characteristic of the wearer.

15. A device for improving a seals interface between a respiration mask and a face of a wearer, the device comprising:
a seal body having a first side that is adapted to face toward facial anatomy of a wearer and that includes an adhesive layer that is adapted to adhere to an epidermis of a user that surrounds only one respiration flow passage and a second side that is opposite the first side and configured to engage a perimeter edge of a mask such that the seal body extends in a continuous manner about a perimeter edge of the mask and overlays at least a portion of the anatomy of the wearer that is oriented inboard of the perimeter edge of the mask to isolate the portion of the anatomy from the respiration flow and a portion of the seal body defines at least one tab that extends at an upper portion of the seal body and is adapted to overlap at least a portion of the wearer's eye socket; and
a backer attached to the first side of the seal body and that removably cooperates with the adhesive layer such that removal of the backer exposes the adhesive for securing the adhesive layer to the epidermis of the user proximate a respiration path opening of the user.

16. The device of claim 15 wherein the seal body is formed of one of a film material, a hydrocolloid material, and a foam material.

17. The device of claim 16 further comprising another backer attached to the second side of the seal body and that removably cooperates with another adhesive associated with the second side of the seal body wherein the another adhesive is configured to selectively adhere to the perimeter edge of the mask.

18. The device of claim 17 wherein at least one of the backer and another backer are split to allow selective exposure of a respective portion of the respective one of the backer and another backer.

19. The device of claim 15 further comprising one of an oral opening shaped to circumferentially surround a mouth of the wearer and a nasal opening and a nasal cutout shaped to overlie a nose and circumferentially surround a nasal opening of the wearer formed by the seal body.

20. The device of claim 15 wherein the seal body is deformable in a thickness direction.

* * * * *